US012796899B2

(12) United States Patent
Xu et al.

(10) Patent No.: US 12,796,899 B2
(45) Date of Patent: Nov. 17, 2026

(54) SEGMENTED BENDING SECTION ASSEMBLY FOR DISPOSABLE URETEROSCOPE

(71) Applicant: HANGZHOU XINZEYUAN MEDICAL TECHNOLOGY CO., LTD., Hangzhou (CN)

(72) Inventors: Yongbin Xu, Hangzhou (CN); Qiurong Wang, Hangzhou (CN); Haijun Ye, Hangzhou (CN); Yanan Cao, Hangzhou (CN); Hao Chi, Hangzhou (CN); Wei Wan, Hangzhou (CN)

(73) Assignee: HANGZHOU XINZEYUAN MEDICAL TECHNOLOGY CO., LTD., Hangzhou (CN)

( * ) Notice: Subject to any disclaimer, the term of this patent is extended or adjusted under 35 U.S.C. 154(b) by 330 days.

(21) Appl. No.: 18/224,894

(22) Filed: Jul. 21, 2023

(65) Prior Publication Data

US 2025/0025026 A1 Jan. 23, 2025

(51) Int. Cl.
*A61B 1/005* (2006.01)
*A61M 25/01* (2006.01)
(Continued)

(52) U.S. Cl.
CPC .......... *A61B 1/0055* (2013.01); *A61B 1/0057* (2013.01); *A61M 25/0138* (2013.01); *A61B 1/00103* (2013.01); *A61B 1/307* (2013.01)

(58) Field of Classification Search
CPC . A61B 1/0055; A61B 1/00103; A61B 1/0057; A61B 1/307; A61B 1/0011;
(Continued)

(56) References Cited

U.S. PATENT DOCUMENTS

2015/0313450 A1* 11/2015 Wieth .................. A61B 1/0057 600/146
2016/0029878 A1* 2/2016 Yamazaki ............ A61B 1/0057 600/149
(Continued)

FOREIGN PATENT DOCUMENTS

CN 207721790 U 8/2018
CN 209847126 U 12/2019
(Continued)

OTHER PUBLICATIONS

CN Office Action for Application No. 202210492550.4, dated Jul. 30, 2025.

*Primary Examiner* — Michael J Carey
*Assistant Examiner* — Olivia Grace Starkey
(74) *Attorney, Agent, or Firm* — Troutman Pepper Locke LLP

(57) ABSTRACT

Provided is a segmented bending section assembly for a disposable ureteroscope, including a bending sectional tube, elastic tubes, and traction cables. Multiple U-shaped limiting grooves arranged in an axial direction of the bending sectional tube are formed in a side wall of a tail portion of the bending sectional tube. An end portion of each of the elastic tubes abuts against a bottom wall of each U-shaped limiting groove, a side wall of the elastic tube abuts against an inside wall of the U-shaped limiting groove, and the elastic tube is welded to the U-shaped limiting groove. A tube body of the bending sectional tube is internally provided with multiple wire-passing channels for the traction cables to pass through, and the traction cable penetrates through the elastic tube and the wire-passing channel and then are fixedly connected to a front end of the bending sectional tube.

4 Claims, 4 Drawing Sheets

(51) Int. Cl.
*A61B 1/00* (2006.01)
*A61B 1/307* (2006.01)

(58) Field of Classification Search
CPC ..... A61B 1/0051; A61B 1/0056; A61B 1/005; A61M 25/0138
See application file for complete search history.

(56) References Cited

U.S. PATENT DOCUMENTS

| | | | | |
|---|---|---|---|---|
| 2021/0378648 | A1* | 12/2021 | Thissen | A61B 17/29 |
| 2023/0069698 | A1* | 3/2023 | Hallauer | A61B 1/0052 |
| 2024/0122458 | A1* | 4/2024 | Fuchs | A61B 1/0055 |
| 2024/0407772 | A1* | 12/2024 | Gafford | A61M 25/0138 |

FOREIGN PATENT DOCUMENTS

| | | |
|---|---|---|
| CN | 112515613 A | 3/2021 |
| CN | 214342219 | 3/2021 |

* cited by examiner

SEGMENTED BENDING SECTION ASSEMBLY FOR DISPOSABLE URETEROSCOPE

TECHNICAL FIELD

The present disclosure refers to the technical field of medical devices, and in particular to a segmented bending section assembly for a disposable ureteroscope.

BACKGROUND

Endoscope generally refers to medical instruments that enter the human body through various pipelines for observing the internal conditions of the human body. The use of endoscope makes it possible to see lesions that cannot be shown by X-rays, so it is very useful for physicians. For example, by means of endoscopes, physicians can observe ulcers or tumors in the stomach and develop the best treatment schedule according to the result of observation. Some endoscopes also have therapeutic functions, such as urology, bronchoscopy, gastroscopy, colonoscopy, laparoscopy.

The existing endoscope body is internally provided with a bending sectional tube, and the bending and steering of a head of the endoscope can be achieved by pulling a steel cable connected to the bending sectional tube. The bending sectional tube is configured to drive the endoscope body to bend and steer through the pulling of the steel cable. However, during the welding of the elastic tube to the existing bending sectional tube, the elastic tube is welded to an inner wall surface of the tail of the bending sectional tube. Due to narrow space in the bending sectional tube, the position of the elastic tube during being welded is inaccurate, and the welding is time-consuming and labor-consuming, resulting in high scrap rate. During the use of the bending sectional tube, the deviation of the position of the elastic tube leads to a deviation of the bending sectional tube during being pulled through the traction rope, and the bending sectional tube often cannot reach the required bending angle, which affects the use of the endoscope.

SUMMARY

In order to overcome the disadvantages in the prior art, a segmented bending section assembly for a disposable ureteroscope is provided.

The technical solution adopted by the present disclosure to solve the technical problem is as follows: A segmented bending section assembly for a disposable ureteroscope includes a bending sectional tube, elastic tubes, and traction cables. Multiple groups of steering notches are formed in a side wall of the bending sectional tube, steering notches in a same group are distributed in an axial direction of the bending sectional tube, and steering notches in different groups are provided on the side wall of the bending sectional tube in a staggered manner. Multiple U-shaped limiting grooves arranged in an axial direction of the bending sectional tube are formed in a side wall of a tail portion of the bending sectional tube. The elastic tubes penetrate into the tail portion of the bending sectional tube, an end portion of each of the elastic tube abuts against a bottom wall of a corresponding one of the multiple U-shaped limiting grooves, a side wall of each of the elastic tubes abuts against an inside wall of the corresponding one of the multiple U-shaped limiting grooves, and an outer diameter of each of the elastic tubes is greater than a width of the corresponding one of the multiple U-shaped limiting grooves. Each of the elastic tubes is welded to the corresponding one of the multiple U-shaped limiting grooves. A tube body of the bending sectional tube is internally provided with multiple wire-passing channels for the traction cables to pass through, and each of the traction cables penetrates through a corresponding one of the elastic tubes and a corresponding one of the multiple wire-passing channels and then are fixedly connected to a front end of the bending sectional tube.

When the elastic tubes are welded and assembled, an end face of each of the elastic tubes abuts against the bottom wall of a corresponding one of the multiple U-shaped limiting grooves, so as to achieve precise positioning, improve machining efficiency and reduce a scrap rate. Each of the elastic tubes can be embedded in a corresponding one of the multiple U-shaped limiting grooves, which not only can increase a space for welding, but also can improve the welding strength.

The steering notches on the side wall of the bending sectional tube can be directly formed by performing laser cutting on a hollow tube by precision laser cutting equipment, and the machining efficiency is high. Each of the traction cables penetrates through a corresponding one of the elastic tubes and a corresponding one of the multiple cable-passing channels and then is welded and connected to the front end of the bending sectional tube. As the elastic tubes are in a precise position, the traction cables are ensured to be in a precise position. By pulling one of the traction cables, one of the multiple groups of steering notches are contracted and another of the multiple groups steering notches are opened, thus making the bending sectional tube reach a suitable bending angle. The elastic tubes and the multiple cable-passing channels are mainly used to protect the traction cables and prevent the traction cables from being stuck or entangled with each other.

Furthermore, in order to prevent one of the traction cables from being blocked by the bottom wall of a corresponding one of the multiple U-shaped limiting grooves when penetrating into the bending sectional tube from a corresponding one of the elastic tubes, a thickness of an overlapping portion between of the end portion of each of the elastic tubes and the bottom wall of the corresponding one of the multiple U-shaped limiting grooves is smaller than a thickness of the side wall of each of the elastic tubes.

Furthermore, each of the multiple cable-passing channels includes multiple cable-passing holes, and the multiple cable-passing holes are formed by punching the side wall of the bending sectional tube towards an inner side of the bending sectional tube. One of the traction cables passes through the whole bending sectional tube, and a movable range of the one of the traction cables is limited through a corresponding one of the multiple cable-passing holes, thus preventing the one of the traction cables from interfering with other parts inside the bending sectional tube when used.

Furthermore, a spacing between two adjacent steering notches in a same group gradually increases from the front end to the tail end of the bending sectional tube, so that requirements of different steering and bending amplitudes at different positions of the tube body of the bending sectional tube are satisfied.

Furthermore, both ends of each of the multiple groups of the steering notches are provided with flared portions, which can increase deformation of the multiple groups of steering notches and reduce stress concentration.

The present disclosure has the beneficial effects that: In accordance with the segmented bending section assembly for a disposable ureteroscope provided by the present disclosure, when the elastic tubes are welded and assembled, an end face of each of the elastic tubes abuts against the bottom wall of a corresponding one of the multiple U-shaped limiting grooves, so as to achieve precise positioning, improve machining efficiency and reduce the scrap rate. Each of the elastic tubes can be embedded in a corresponding one of the multiple U-shaped limiting grooves, which not only can increase a space for welding, but also can improve the welding strength. As the elastic tubes are in a precise position, the traction cables are ensured to be in a precise position, and the bending sectional tube can reach a suitable bending angle by pulling one of the traction cables.

BRIEF DESCRIPTION OF THE DRAWINGS

The present disclosure is further described below with reference to the accompanying drawings and exemplary embodiments.

Figure 1:
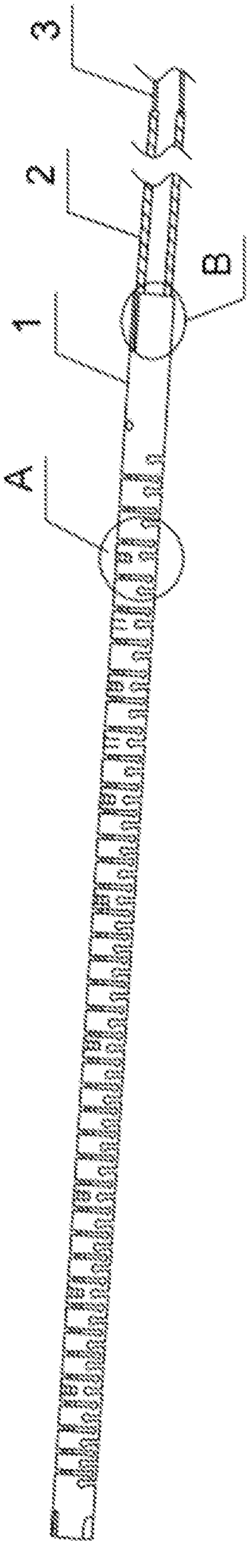
FIG. 1 is a structural schematic diagram of an optimal embodiment of the present disclosure.

Reference signs in the drawings: 1—bending sectional tube, 11—steering notch, 111—flared portion, 12—U-shaped limiting groove, 121—bottom wall of U-shaped limiting groove, 122—inside wall of U-shaped limiting groove, 13—cable-passing hole, 2—elastic tube, 3—traction cable.

DETAILED DESCRIPTION

The present disclosure is further described below with reference to the accompanying drawings and exemplary embodiments. This figure is a simplified schematic diagram illustrating only the basic structure of the present disclosure in a schematic manner, and therefore showing only the configuration related to the present disclosure.

Figure 2:
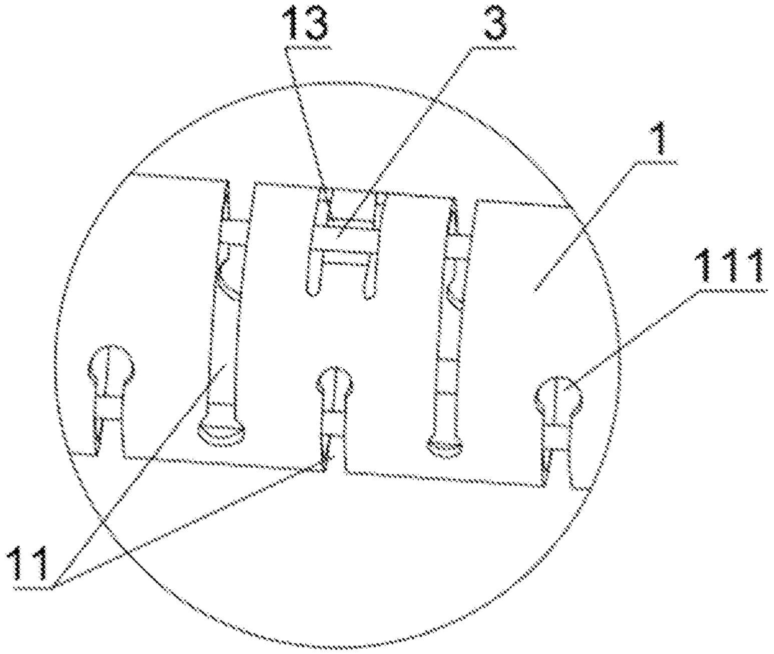
FIG. 2 is an enlarged view of section A in FIG. 1.
Figure 3:
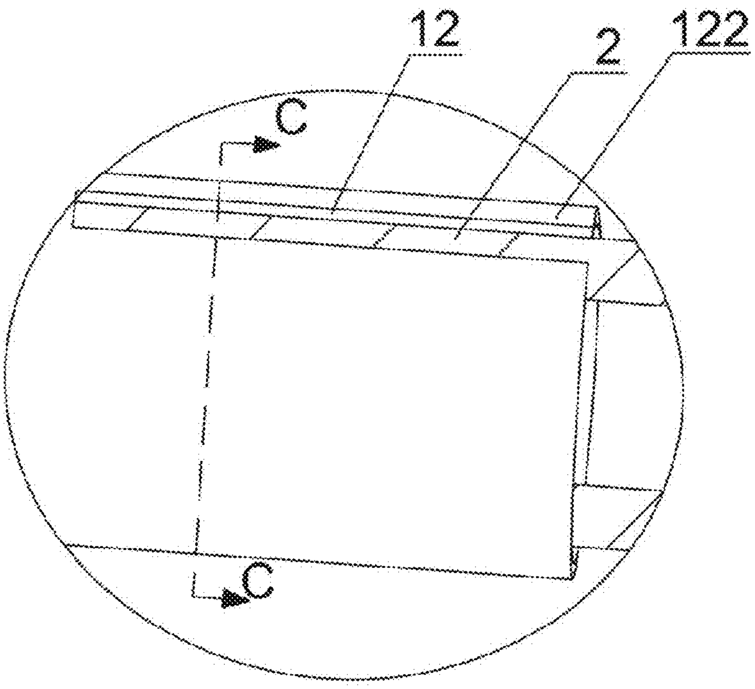
FIG. 3 is an enlarged view of section B in FIG. 1.
Figure 4:
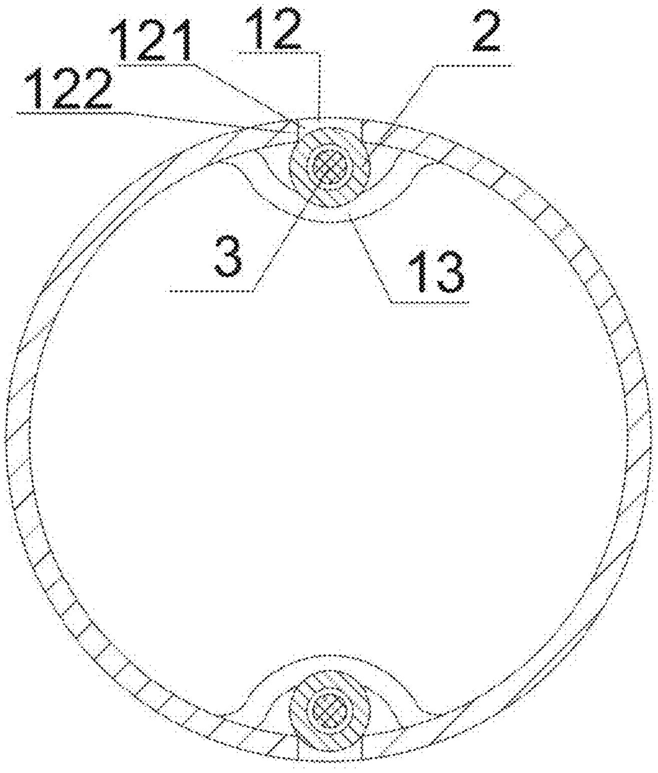
FIG. 4 is a sectional schematic diagram of FIG. 3 taken along a line C-C.

As shown in FIGS. 1-4, a segmented bending section assembly for a disposable ureteroscope of the present disclosure includes a bending sectional tube 1, elastic tubes 2, and traction cables 3. Two groups of steering notches 11 are formed in a side wall of the bending sectional tube 1, and both ends of the steering notch 11 are provided with flared portions 111. The steering notches 11 in a same group are distributed in an axial direction of the bending sectional tube 1, and the steering notches in different groups are provided on the side wall of the bending sectional tube 1 in a staggered manner. Two U-shaped limiting grooves 12 arranged in an axial direction of the bending sectional tube 1 are formed in a side wall of a tail portion of the bending sectional tube 1. The elastic tube 2 penetrates through the tail portion of the bending sectional tube 1, an end portion of the elastic tube 2 abuts against a bottom wall 121 of the U-shaped limiting groove 12, a side wall of the elastic tube 2 abuts against an inside wall 122 of the U-shaped limiting groove 12, and an outer diameter of the elastic tube 2 is greater than a width of the limiting groove. The elastic tube 2 is welded to the U-shaped limiting groove 12. A tube body of the bending sectional tube 1 is internally provided with two wire-passing channels for the traction cables 3 to penetrate through, and the traction cables 3 penetrate through the elastic tubes 2 and the wire-passing channels and then are fixedly connected to a front end of the bending sectional tube 1.

A thickness of an overlapping portion between the end portion of the elastic tube 2 and the bottom wall 121 of the U-shaped limiting groove 12 is less than that of the side wall of the elastic tube 2.

The cable-passing channel includes multiple cable-passing holes 13, and the cable-passing holes 13 are formed by punching the side wall of the bending sectional tube towards an inner side of the bending sectional tube 1.

A spacing between two adjacent steering notches 11 in the same group gradually increases from the front end to the tail end of the bending sectional tube 1.

The machining process of the segmented bending section assembly for a disposable ureteroscope is described below.

A hollow tube is selected and subjected to direct laser-cut by precision laser cutting equipment to obtain steering notches 11 and U-shaped limiting grooves 12, and then the side wall of a bending sectional tube 1 are punched towards the inner side of the bending sectional tube 1 to obtain cable-passing holes 13. The elastic tubes 2 abut against and then are welded to the U-shaped limiting grooves 12, so that the precise positioning is achieved, the machining efficiency is improved, and the scrape rate is reduced. Meanwhile, the space for welding is increased, and the welding strength is improved. One traction cable 3 corresponds to one elastic tube 2 and one cable-passing channel, and the traction cable 3 penetrates through the elastic tube 2 and the cable-passing holes 13 in sequence and then extends to the front end of the bending sectional tube 1 to be welded to the front end of the bending sectional tube 1, thus completing assembly of the segmented bending section assembly for a disposable ureteroscope.

The directions and references in the present disclosure (e.g., up, down, left, right, etc.) may only be used to aid in the description of the features in the drawings. Accordingly, the following specific embodiments are not taken in a limiting sense, and the scope of the claimed subject matter is limited only by the appended claims and their equivalents.

With the above ideal embodiment according to the present disclosure as an inspiration, those skilled in the art can make various changes and modifications without departing from the scope of the present disclosure through the above description. The technical scope of the present disclosure is not limited to the contents in the specification, but must be determined according to the scope of the claims.

What is claimed is:

1. A segmented bending section assembly for a disposable ureteroscope, comprising:

a bending sectional tube, wherein a plurality of groups of steering notches are formed in a side wall of the bending sectional tube, a first group of steering notches are distributed in an axial direction of the bending sectional tube, a second group of steering notches and the first group of steering notches are provided on the side wall of the bending sectional tube in a staggered manner, a plurality of U-shaped limiting grooves arranged in the axial direction of the bending sectional tube are formed in a side wall of a tail portion of the bending sectional tube;

elastic tubes, wherein the elastic tubes penetrate into the tail portion of the bending sectional tube, an axial end portion of each of the elastic tubes abuts against a bottom wall of a corresponding one of the plurality of U-shaped limiting grooves, a side wall of the each of the elastic tubes abuts against an inside wall of the corresponding one of the plurality of U-shaped limiting grooves, and an outer diameter of the each of the elastic tubes is greater than a width of the corresponding one of the plurality of U-shaped limiting grooves; the each of the elastic tubes is welded to the corresponding one of the plurality of U-shaped limiting grooves; and traction cables, wherein a tube body of the bending sectional tube is internally provided with a plurality of wire-passing channels for the traction cables to pass through, and each of the traction cables penetrates through a corresponding one of the elastic tubes and a corresponding one of the plurality of wire-passing channels and then are fixedly connected to a front end of the bending sectional tube which is opposed to the tail portion of the bending sectional tube, wherein each of the plurality of U-shaped limiting grooves is closed at one end thereof by the bottom wall and open at an opposite end thereof in the axial direction of the bending sectional tube, and wherein the one end of the each of the plurality of U-shaped limiting grooves is provided to be away from an end face of the tail portion of the bending sectional tube, the end face is away from the front end of the bending sectional tube in the axial direction of the bending sectional tube, and the opposite end of the each of the plurality of U-shaped limiting grooves is provided on the end face of the tail portion of the bending sectional tube.

2. The segmented bending section assembly for a disposable ureteroscope according to claim 1, wherein each of the plurality of wire-passing channels comprises a plurality of wire-passing holes, and the plurality of wire-passing holes are formed by punching the side wall of the bending sectional tube toward an inner side of the bending sectional tube.

3. The segmented bending section assembly for a disposable ureteroscope according to claim 1, wherein a spacing between two adjacent steering notches in a same group gradually increases from the front end of the bending sectional tube to a tail end of the bending sectional tube.

4. The segmented bending section assembly for a disposable ureteroscope according to claim 1, wherein both ends of each steering notch are provided with flared portions.

* * * * *